United States Patent [19]

Llop

[11] 3,983,390
[45] Sept. 28, 1976

[54] DEVICE FOR MEASURING ANGULAR DEVIATION OF A LIGHT BEAM BY USE OF GRATINGS

[75] Inventor: Helenio Llop, Montreuil, France

[73] Assignee: Societe d'Optique, Precision Electronique et Mechanique Sopelem, Paris, France

[22] Filed: June 6, 1975

[21] Appl. No.: 584,496

[30] Foreign Application Priority Data
June 12, 1974 France .............................. 74.20285

[52] U.S. Cl. ........................ 250/231 R; 250/237 G; 356/128; 356/169
[51] Int. Cl.² .......................................... G01D 5/34
[58] Field of Search ........... 250/231, 237 R, 237 G; 356/169, 170, 128, 134

[56] References Cited
UNITED STATES PATENTS

| | | | |
|---|---|---|---|
| 3,371,335 | 2/1968 | Seewald | 356/169 |
| 3,427,463 | 2/1969 | Weyrauch | 250/237 G |
| 3,451,054 | 6/1969 | Johnson | 356/169 |
| 3,586,665 | 6/1971 | Weyrauch | 356/169 |
| 3,728,715 | 4/1973 | Shapiro | 250/237 G |

Primary Examiner—David C. Nelms
Attorney, Agent, or Firm—Haseltine, Lake & Waters

[57] ABSTRACT

A measuring device includes means for producing an image of a transmitting diffraction grating, means for shifting the image by an amount related to the quantity to be measured, and a receiving diffraction grating for measuring the shift of the image. Each diffraction grating includes a plurality of tracks of increasing pitch, each track of the transmitting grating having a corresponding track on the receiving grating. The device may form a refractometer.

9 Claims, 6 Drawing Figures

FIG:1

FIG:3
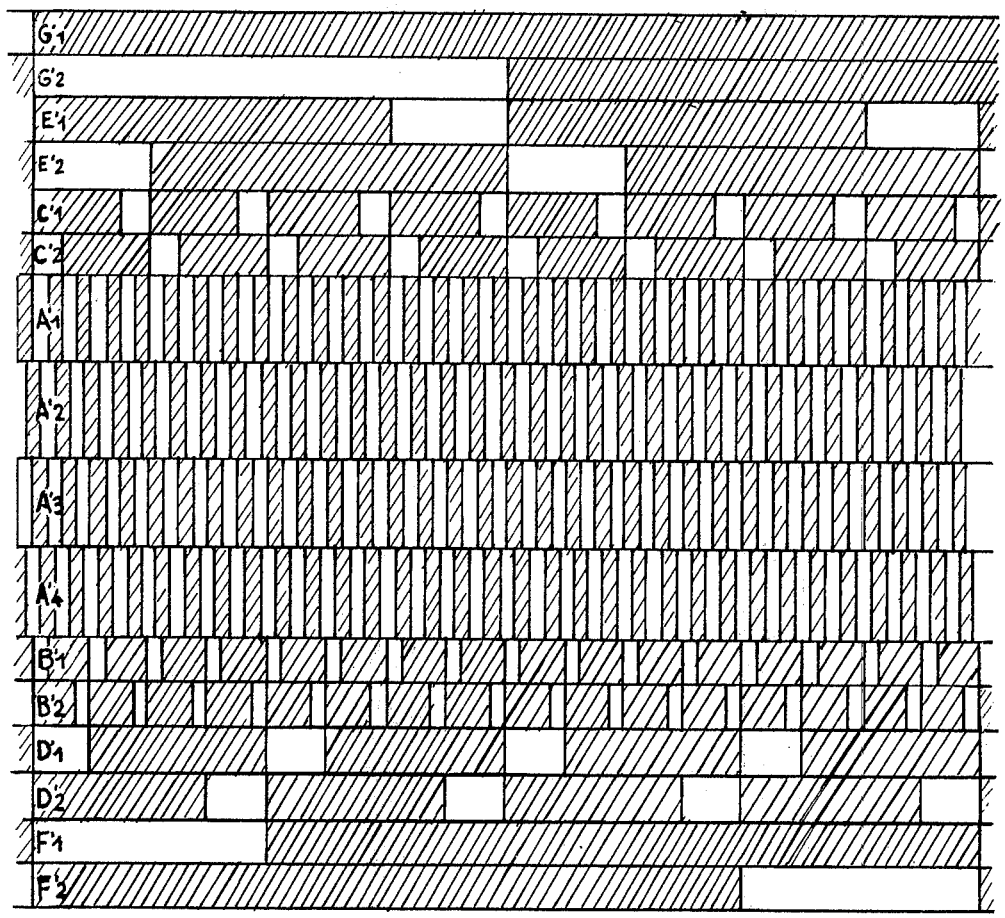

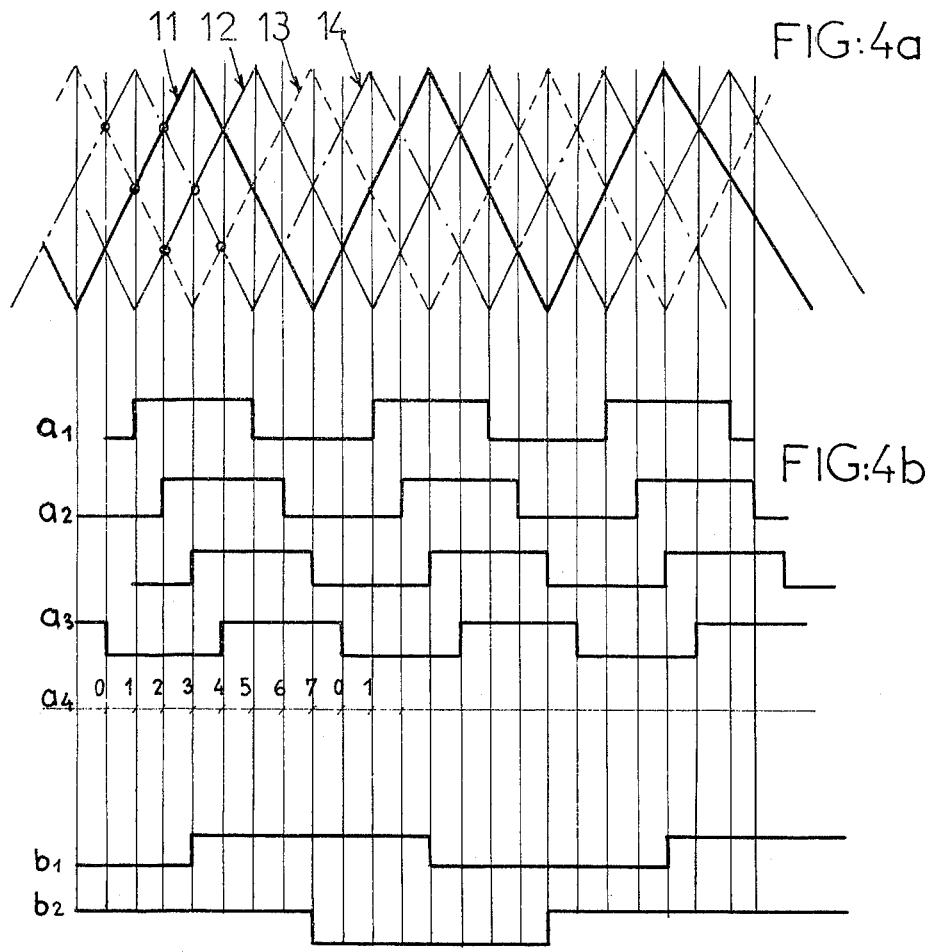

DEVICE FOR MEASURING ANGULAR DEVIATION OF A LIGHT BEAM BY USE OF GRATINGS

The invention is concerned with an instrument for measuring small deviations, for example refractometers.

A refractometer is used to measure the deviation between the refractive index of a body and a reference index and normally it comprises a prism which is illuminated by a light beam. Often one wishes to determine the refractive index of a liquid in which case a prismatic vessel is used and the liquid is placed inside it. A deviatory system is thus produced which is interposed in the path of the light beam, and the deviation of the light beam after divergence by the body under examination, is measured. Refractometers exist in which measurement of the deviation is made by means of a deffraction grating. The light beam is produced by a slit, the image of which is formed on a coded scale of the grating. A photo cell system is provided to indicate the position of the slit image along the scale, and a system for analysing the signals provided by the photo cells can give the deviation which one is endeavouring to measure by direct reading.

In known instruments, therefore, accurate measurement depends on the width of the slit, and the fineness of the engraved pitch of the defraction grating because the latter establishes the increment of measurement. Furthermore, as the deviation is measured directly on the scale, the useful length of the latter is equal to the maximum deviation one is able to measure. Now the deviation is often extremely minute. Short coded scales must therefore be used on which it would be difficult to draw a large number of lines.

The invention is concerned with a new instrument an embodiment of which enables these disadvantages to be overcome.

According to the present invention there is provided an instrument for measuring small deviations, comprising: a device for sending a luminous beam along an optical axis; a means for moving the beam in relation to the optical axis depending on the deviation to be measured, a receiving diffraction grating for the beam comprising a multiplicity of tracks of recurring transparent areas, the tracks increasing in pitch from one to the other; and a unit for detecting beam movement relative to the tracks the beam sending device comprises a light source and a transmitting diffraction grating, the image of which is projected onto the receiving diffraction grating the transmitting grating comprising a plurality of tracks, each track of the transmitting grating corresponding to a track of the receiving grating, corresponding tracks having corresponding pitches.

The invention will be better understood from the following description of a preferred embodiment thereof, given by way of example only, reference being had to the accompanying drawings, wherein:

FIG. 3 is an example of the receiving diffraction grating.

FIGS. 4a, 4b, and 4c respectively illustrate diagrammatically the wave signals produced by the detectors, the corrected signals enabling measurements to be taken, and the transcribing matrix for the coded measuring system used.

Figure 1:
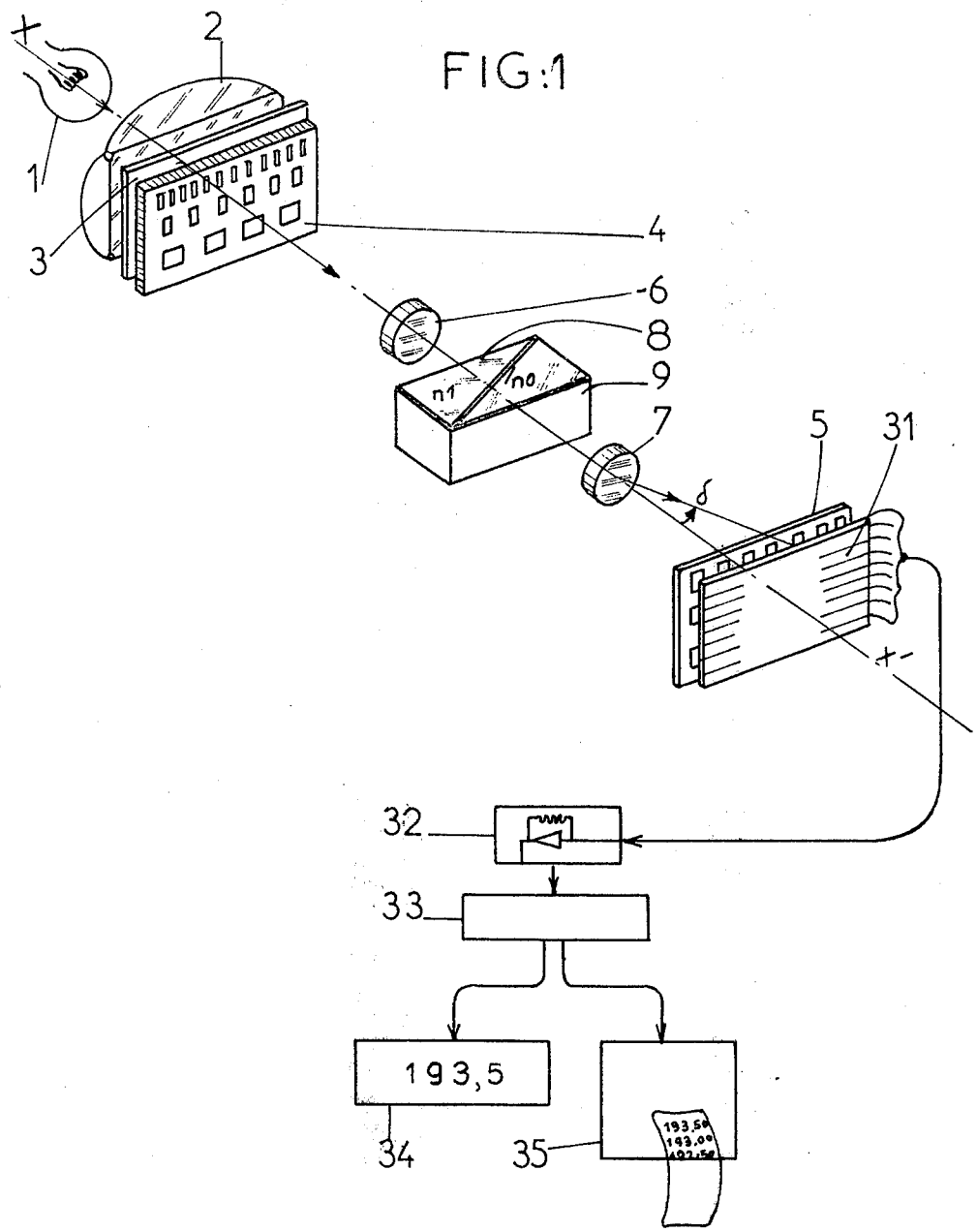
FIG. 1 is a diagrammatic layout of an embodiment of instrument according to the invention.

The instrument illustrated diagrammatically in FIG. 1 comprises a light source 1 which illuminates a transmitting diffraction grating 4, via a condenser 2 and a filter 3. The image from this diffraction grating is projected onto a receiving diffraction grating 5 by means of two lenses 6 and 7 and passes through two prismatic vessels 8, 9 arranged side by side. One of the vessels 8,9 determines a reference index, the other vessel having an index the divergence of which from the reference index is to be measured, the said divergence determining a deviation δ of a light beam from the optical axis X—X′. Light passing through diffraction grating 5 falls on a detector unit 31 which comprises a multiplicity of photosensitive cells made up of bands, each band being located in front of a track of the receiving diffraction grating. Signals sent out by the photosensitive cells are received by an analyzing system comprising electronic correcting circuits 32 and transcribing circuits 33 which give the value measured either on a display panel 34 or in the form of a print-out 35. On similar devices up to the present time the movement of a slit image along each track of the receiving grating has been measured. Thus only a length of track equal to the maximum divergence of the image of the slit on either side of the optical axis was used. As this maximum divergence was usually small in relation to the instrument field, each track only covered part of the said field.

Furthermore, as each track was only illuminated by a single slit image only a small portion of light energy emitted by source 1 was used.

On the other hand, in the instrument shown in FIG. 1 measurement is made by moving the image of a diffraction grating track along each track of the receiving grating. The track images are produced by transmitting diffraction grating 4 which accordingly comprises a multiplicity of engraved tracks each one of which corresponds to a track on the receiving diffraction grating. Opposite tracks correspond to one another and in the usual instance where the system will have a magnification of × 1, opposite paths will have identical pitches. In the simplest method of application, illustrated in FIG. 1, transmitting diffraction grating 4 will be identical to receiving diffraction grating 5.

Figure 2:
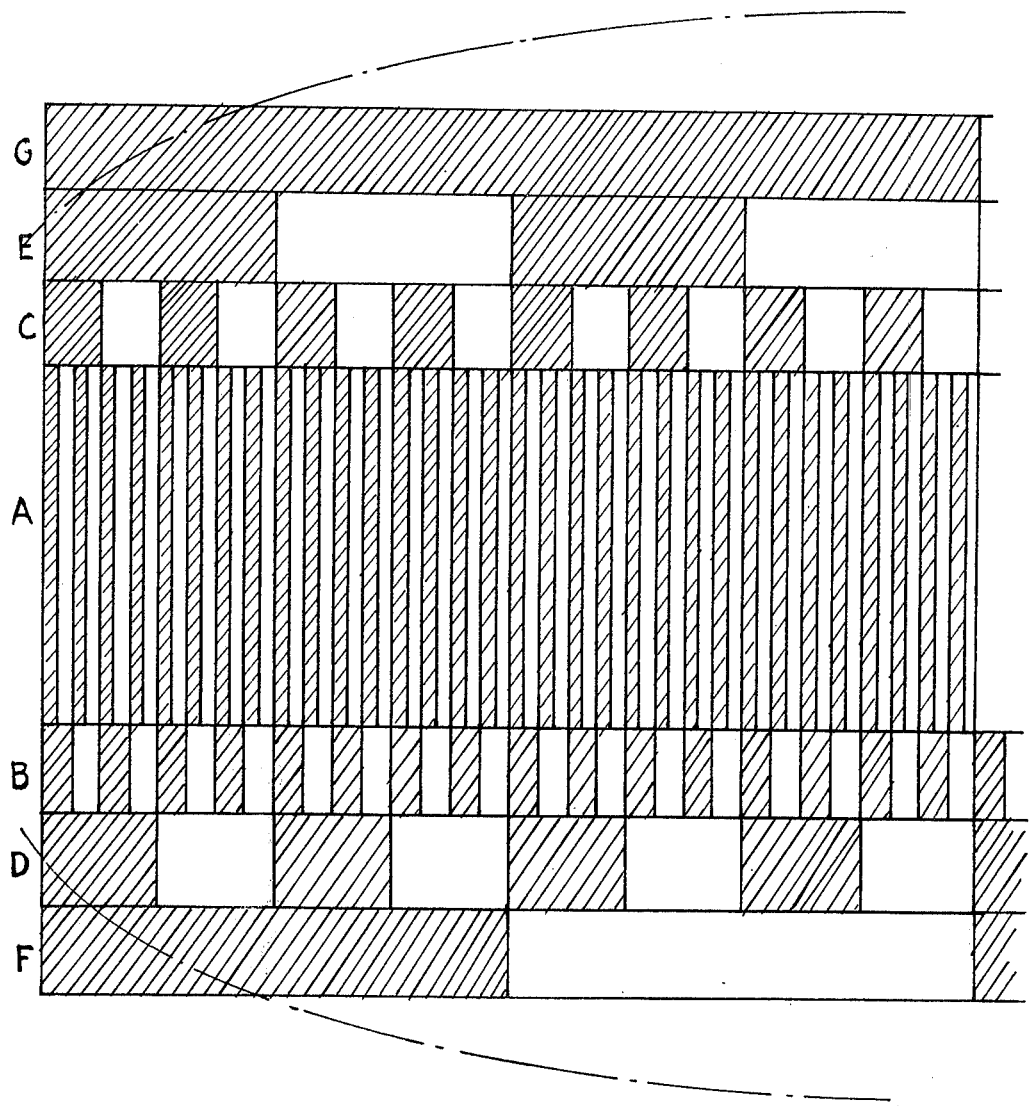
FIG. 2 is an example of the transmitting diffraction grating used in the instrument of FIG. 1.

Using the instrument of FIG. 1 measurement is made in a manner totally different from that in earlier systems in that instead of measuring the movement of a slit image across grating 5, the movement of a diffraction grating image relative to grating 5 is measured. Referring to FIG. 2, it will be understood that when there is not deviation, the transmitting grating image is precisely superimposed on the receiving grating, each transparent area on the transmitting diffraction grating being aligned with a transparent area on the receiving diffraction grating. When the transmitting grating image is superimposed on the receiving grating in this manner the detector 31 receives the maximum amount of light and sends signals of maximum amplitude. If the transmitting grating image and the receiving grating are offset to such an extent that no light falls on the detector the signals sent out by the detector are at their minimum amplitude.

When there is a slight deviation of the refracted beam the image of the transmitting diffraction grating moves in one direction or the other in relation to the receiving grating. The dark areas of the transmitting diffraction grating image thus partially cover the transparent areas of the receiving grating and the amplitude of the signals sent out by detector 31 decreases. When the image of the transmitting diffraction grating has moved a distance corresponding to one half the pitch of the finest track, the transparent areas of the finest track of the receiving grating are covered by the dark areas of the image of the finest track of the transmitting grating and the signal sent out by the photo cell bank corresponding to the finest track is at its minimum amplitude. The same process takes place for each track on the receiving grating each time that the image of the corresponding track of the transmitting grating moves one half the pitch of that track. Thus wave signals are obtained of a pitch equal to that of the corresponding track by movement of the two gratings one in front of the other and the combinaton of which enables measurement of the deviation of the transmitting grating image to be obtained in known manner. The system which has just been described offers considerable advantages over earlier known systems. Instead of moving a slit image along each track of the receiving grating the full length of each track is continually illuminated. Thus a stronger photoelectric signal is obtained and even for the finest track, all the intervals take part in the measurement. In contrast, in the known system, only those intervals illuminated by the slit image take part. A much more reliable measurement is also obtained because, even if some slits are obscured, for example, by a foreign body on the receiving grating, the measurement is not affected. The use of the whole of the instrument field, which is illustrated in FIGS. 2 and 3, enables a considerable improvement to be obtained.

Indeed, once the field has completely covered the grating the paths will be positioned one in relation to another in the position illustrated in FIG. 2. Path A, with the lowest denomination, for example $2^0$, will be placed in the center of the grating. Path B with the next lowest denomination, that is $2^1$, will be placed alongside path A and path C with a denomination of $2^2$ will be placed on the other side of path A. Path D with a denomination of $2^3$ will be placed alongside path B and path E with a denomination of $2^4$ will be placed alongside path C. According to the number $n$ of paths used, the said paths will continue to be placed alternately alongside each other on either side of path A, progressively further away from the grating. Thus a number of paths are placed so that the desired range of measurement equals $2^n$. This arrangement, which is possible due to the fact that the whole of the field is used, enables the finest paths to be placed in the center of the field, that is to say in a position where the risks of distortion are lowest. In contrast, paths with the longest pitches are found along the top and bottom edges, thus there is no risk of them being able to introduce errors in measurement if they are incomplete or distorted.

Furthermore, the length of the tracks of the coded scale will be, to advantage, several times greater than the deviation to be measured, thus enabling engraving errors in the transmitting and receiving gratings to be averaged out. Precision is not a major factor in the top and bottom tracks with the greatest pitches thus their length can be reduced to the deviation to be measured. In this way, the centering of the tracks along the optical axis enables all the paths on the coded scale to lie within a circular field as shown in dotted outline in FIG. 2. To simplify the illustrations only the center part of the coded scales have been illustrated and the number of paths has been reduced. For this reason the field, distorted by anamorphosis, is shown diagrammatically in the form of an elliptical curve.

In the instrument described above, the receiving diffraction grating 5 comprises tracks which correspond each to each, both in position and dimensions, to corresponding tracks of the transmitting grating 4. It might be considered desirable to make the transparent areas narrower than the dark areas, particularly on paths of high denomination, the important part being that each receiving grating track has a pitch identical to that of a corresponding path in the transmitting grating. In order to avoid ambiguities in reading, it is advisable to provide two engraved tracks for reading per bed, one offset to the front, the other offset to the rear in relation to the transitions of the track with the lowest denomination. This has been illustrated in FIG. 3, the front and rear offsets for each track being equal to one quarter of the pitch of the preceding track.

FIG. 3 also illustrates another improvement. As can be seen four tracks A'1, A'2, A'3, A'4 on the receiving grating, offset one in relation to the other by a quarter pitch, correspond to track A in the transmitting grating. The four tracks A'1, A'2, A'3, A'4 have the same pitch as track A.

Identical and independent photoelectric detectors are placed behind each track and thus they send wave signals 11, 12, 13, 14 offset one quarter of a period one from the other, as illustrated in FIG. 4a. The signals can be corrected in conventional manner in order to compare them with a constant datum level, however it would be preferable to make an intercomparison in accordance with French Pat. No. 2.082.594 filed on the Mar. 20, 1970.

Thus signals 11, 12, 13 14 are combined differentially between each other by means of differential amplifiers to obtain square formm signals $a1, a2, a3, a4$ illustrated in FIG. 4b, thus:

$a1 = (11) - (13)$
$a2 = (11) - (14)$
$a3 = (12) - (14)$
$a4 = (13) - (14)$

Note that for one engraved pitch on the finest denomination track one could obtain:

two data presentations using signal ($a1$) only,
four data presentations using and combining signals ($a1$) and ($a3$),
eight data presentations using and combining signals ($a1$), ($a2$), ($a3$) and ($a4$).

Thus, all in one and the same application, it is possible to obtain three grades of precision depending on the way the signals are used. In FIG. 4c the matrix for transcribing has been given which enables signals $a1, a2, a3, a4$ to be converted into eight digital figures ranging from 0 to 7.

In FIG. 4d, signals b1 and b2 are illustrated, these are sent by tracks B'1 and B'2 and in consequence are offset one quarter of a pitch to the front and rear of the track with a denomination of $2^0$. No advantage can be gained by illustrating other signals sent from tracks of higher denomination as the analysis of the coded system is carried out in conventional manner.

Neither has it been considered necessary to illustrate the photosensitive cells used. Preferably these will be cells having the exact length and width of the corresponding tracks, however a group of photoelectric cells with small receiving surface such as photodiodes might be used and these could be positioned on the focal plane of the light collectors.

One advantage of the instrument described above is the ability to use gratings which are much wider than the maximum deviation one wishes to measure. As the image of the transmitting grating is able to move one side or the other of the optical axis, the said transmitting grating will be given the maximum width compatible with the instrument field and, if the magnification is × 1, the receiving grating will have a width equal to that of the trasmitting grating, increased, on either side, by the maximum deviation to be measured. Moreover it is not essential that the image of the transmitting grating covers the whole of the receiving grating because, according to an advantage of the invention, the coded paths have a width greater than the deviation measured.

Of course the invention is not limited to the details of the method of application which has just been described, on the contrary, it encompasses all variations, particularly those which differ only in respect of the use of equivalent methods. For example, while the invention as been described with reference to an instrument with a magnification of × 1, the invention applies also to other examples, the corresponding tracks of the transmitting and receiving gratings requiring only homothetic pitches in a ratio equal to the magnification.

Then again the invention has been described as a refractometer, in its application. However the same principle may be applied for the realisation of other instruments intended for measuring deviations of small amplitude. Thus movement of the transmitting grating image may take place as a result of mechanical movement of the grating instead of arising from divergence of the beam image through a prism, the transmitting grating in this case being in contact with the receiving grating.

Also the optical divergence of the luminous beam may be obtained by rotating a mirror as in many types of know instruments.

What is claimed is:

1. An instrument for measurement of angular deviations comprising a luminous source for projecting a luminous beam along an optical axis, means for angularly displacing the beam with respect to the optical axis as a function of the angular deviation to be measured, a transmitting diffraction grating interposed between said source and said beam displacing means and having tracks of recurrent transparent areas for producing an image with a given transverse field, a receiving diffraction grating disposed downstream of the beam displacing means for receiving said image of the transmitting diffraction grating thereon, and means for detecting displacement of the image of the transmitting grating on the receiving grating, said image covering substantially the entire extent of the receiving grating, said gratings being centered on said optical axis and each being constituted by a plurality of engraved track arrangements, the image of each track arrangement of the transmitting grating being projected onto a corresponding track arrangement of the receiver grating, the corresponding track arrangements having tracks with corresponding spacing, the track arrangements of each grating having stepwise successively increasing spacing between tracks, said gratings extending over the width of the field such that each track is illuminated over the entire length thereof, the width of each track being greater than the displacement corresponding to the maximum angular deviation to be measured.

2. An instrument according to claim 1, forming a refractometer, said means for displacing the beam comprising a prism for deviation of said beam depending on the refractive index of the prism.

3. An instrument according to claim 1, wherein said means for detecting beam displacement comprises a multiplicity of photocell detectors, each positioned adjacent a corresponding track on the receiving grating on the side thereof opposite the side facing the transmitting grating, and means for analyzing the signals sent by the said photocell detectors.

4. An instrument according to claim 3, wherein the photocell detectors corresponding to the tracks with smallest spacing are elongate and extend substantially the full length of such tracks.

5. An instrument according to claim 3, wherein the photocell detectors corresponding to the tracks with smallest spacing each extend along a length equal to the length of such tracks less the value of the movement corresponding to the maximum deviation to be measured.

6. An instrument according to claim 1, having unity magnificaton, said transmitting and receiving gratings have similar tracks of identical spacing.

7. An instrument according to claim 1, wherein the track arrangement with the smallest spacing is located in the center of the grating and the track arrangements with greater spacing are placed alternately on either side of the center track.

8. An instrument according to claim 1, wherein the track arrangement of the receiving grating with the smallest spacing is subdivided into n tracks of the same spacing, offset in relation to one another by a fraction 1/n of the spacing of said tracks, said detecting means comprising a photocell detector for each offset track, the assembly of the said offset tracks having a total width substantially equal to the width of the corresponding track of the same spacing on the transmitting grating.

9. An instrument according to claim 8, comprising means for analyzing recurring signals sent out by the photocell detectors comprising means for producing corrected signals by differential combination of the said recurring signals.

* * * * *